US00PP17780P3

(12) United States Plant Patent
Werner et al.

(10) Patent No.: US PP17,780 P3
(45) Date of Patent: Jun. 5, 2007

(54) PEACH TREE NAMED 'CAROLINA GOLD'

(50) Latin Name: *Prunus persica*
Varietal Denomination: Carolina Gold

(75) Inventors: Dennis James Werner, Raleigh, NC (US); Layne Karlton Snelling, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/993,713

(22) Filed: Nov. 22, 2004

(65) Prior Publication Data

US 2006/0112470 P1 May 25, 2006

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent Bell
*Assistant Examiner*—June Hwu

(57) ABSTRACT

*Prunus persica* (L.) Batsch 'Carolina Gold' is a new and distinct variety of edible peach tree that has the following unique combination of desirable features that are outstanding in a new variety.

1. High flower bud chilling (cold) requirement resulting in later flowering relative to many other commercial varieties of peach.
2. Flower buds which demonstrate a high level of resistance to cold temperature injury.
3. Firm, yellow flesh fruit with excellent flavor and aroma, and flesh that is resistant to browning after slicing.
4. Heavy and regular bearing of large size fruit, up to 3 inches in axial diameter.
5. Fruit with late maturity.
6. Foliage and fruit highly resistant to infection by bacterial spot disease.

6 Drawing Sheets

Latin name of the genus and species: The Latin name of the novel peach tree variety disclosed herein is *Prunus persica* (L.) Batsch.

Variety denomination: The inventive cultivar of *Prunus persica* disclosed herein has been given the variety denomination 'Carolina Gold'.

BACKGROUND OF THE INVENTION

The present invention relates to a new and distinct cultivar of *Prunus persica* (peach) grown as a fruit tree for home use and for commercial agriculture. Peach is typically grown for their edible fruit that are used for fresh consumption, or for home canning.

The new and distinct variety of peach (*Prunus persica* (L.) Batsch) originated as a first generation descendant from a hand pollinated cross of 'Biscoe' peach (non-patented)× NC-C5S-067 made in 1995 at the North Carolina State University Lake Wheeler Field Laboratory in Raleigh, N.C. 'Biscoe' was released and named as a peach cultivar by the North Carolina Agricultural Research Service in 1968, and is available in commerce. The NC-C5S-067 parent used in this hybridization was derived from a hand-pollinated cross of 'Encore' (U.S. Plant Pat. No. 4,572)×'Calanda San Miquel 2383' (non-patented) made in 1988 at the Sandhills Research Station, Jackson Springs, N.C. 'Encore' was named and released as a peach cultivar by Rutgers University in 1980, and assigned U.S. Plant Pat. No. 4,572. 'Calanda San Miquel 2383' is an old land race of peach originating in Spain, with no documented history of release date.

The approximately 160 seeds resulting from the 1995 controlled hybridization were germinated in a greenhouse at North Carolina State University, Raleigh, N.C. in the fall of 1995 and planted in the field in spring of 1996 at the Sandhills Research Station, Jackson Springs, N.C. These trees, growing on their own roots, first produced fruit in 1998, and one seedling, designated NC98-83, was selected for its large yellow flesh fruit, attractive red and yellow skin color, bacterial spot resistance, fruit with high flavor and aroma, late season of ripening, low flesh browning potential, and heavy fruit production. This original plant was growing on its own roots, and demonstrated characteristics identical to those subsequently expressed when propagated on 'Lovell' seedling rootstock.

Plants and fruit of this new variety differ from its parents. The new variety produces yellow flesh fruit that are larger, more round, and firmer than 'Biscoe'. The flesh of this new variety is also resistant to flesh browning after the fruit is sliced for consumption, further distinguishing it from its 'Biscoe' parent. Fruit of this new variety are larger, firmer, and show more red color on the skin than the NC-C5S-067 parent. Bacterial spot resistance of the new variety is superior to that demonstrated by NC-C5S-067 and 'Encore' (U.S. Plant Pat. No. 4,572), based on field observation under conditions of natural disease infection. The round, smooth fruit have nearly equal amounts of attractive red skin color and golden yellow ground color.

During the years 1999 and 2000, the original plant selection was propagated asexually by grafting of vegetative buds onto the standard peach seedling rootstock cultivar 'Lovell'. Four grafted trees of the variety were established in test plots at Sandhills Research Station in 2000, and three additional grafted trees of the variety were established at the same station in 2001.

The new variety has routinely been asexually multiplied by grafting, specifically 'T' budding. It readily forms a graft union with peach 'Lovell' rootstock and resumes normal growth. During all asexual propagation, the characteristics of the original plant have been maintained. Grafted trees on 'Lovell' rootstock exhibit characteristics identical to those of the tree on its own roots, and no aberrant phenotypes have appeared.

Test plantings and performance evaluation over seven years at the Sandhills Research Station demonstrate this variety to be relatively consistent in its characteristics even under the different growing conditions associated with yearly climatic variation.

Plants of the new variety are very vigorous and grow rapidly after establishment of trees in the field. Young trees have averaged 2–3 feet of growth per year. Plants are semi-upright in growth habit. Flowering sometimes occurs in the second year of growth, but more commonly trees begin flowering and fruiting in the third year after establishment. Flowers are single, medium red-purple, small, and non-showy. Flowering usually begins in mid to late March in Jackson Springs, N.C.; the chilling requirement is estimated to be 1000 hours below 4° C., based on comparison of flowering time to known varieties such as 'Contender' (non-patented) and 'Biscoe' (non-patented). Flowering generally lasts for 7–10 days, depending on temperature at time of bloom.

Fertility of flowers is excellent, and fruit set is generally very high in most years. Flowers have shown excellent resistance to cold temperatures during winter dormancy and during flower development in the spring. Fruit are very large, often 3 inches in diameter, yellow fleshed, and highly flavorful and aromatic. Fruit ripen in late July to early August in Jackson Springs, N.C., averaging August 1.

'Carolina Gold' is distinguished from other related known cultivars based on the unique combination of traits including late fruit ripening, high flower bud chilling requirement, resistance to bacterial spot disease, high fruit flesh quality, flower buds resistant to cold weather, large fruit size, and fruit flesh that is resistant to oxidative browning after slicing.

The new variety has been named the Carolina Gold cultivar.

SUMMARY OF THE INVENTION

'Carolina Gold' is a new and distinct variety of edible peach tree that has the following unique combination of desirable features outstanding in a new variety.

1. High flower bud chilling (cold) requirement resulting in later flowering relative to many other commercial varieties of peach.
2. Flower buds that demonstrate a high level of resistance to cold temperature injury.
3. Firm, yellow flesh fruit with excellent flavor and aroma, and flesh that is resistant to browning after slicing.
4. Heavy and regular bearing of large size fruit, up to 3 inches in axial diameter.
5. Fruit with late maturity, typically early August in North Carolina.
6. Foliage and fruit highly resistant to infection by bacterial spot disease.

BRIEF DESCRIPTION OF THE DRAWINGS

The photographs in the drawings were made using conventional film or digital photography techniques, and show the colors as true as reasonably possible by conventional photography. Colors in the photographs may differ slightly from the color values cited in the detailed botanical description, which accurately describe the colors of the new *Prunus persica* variety. All photographs were taken from trees growing at the Jackson Springs, N.C.

DETAILED BOTANICAL DESCRIPTION OF THE VARIETY

Figure 1:
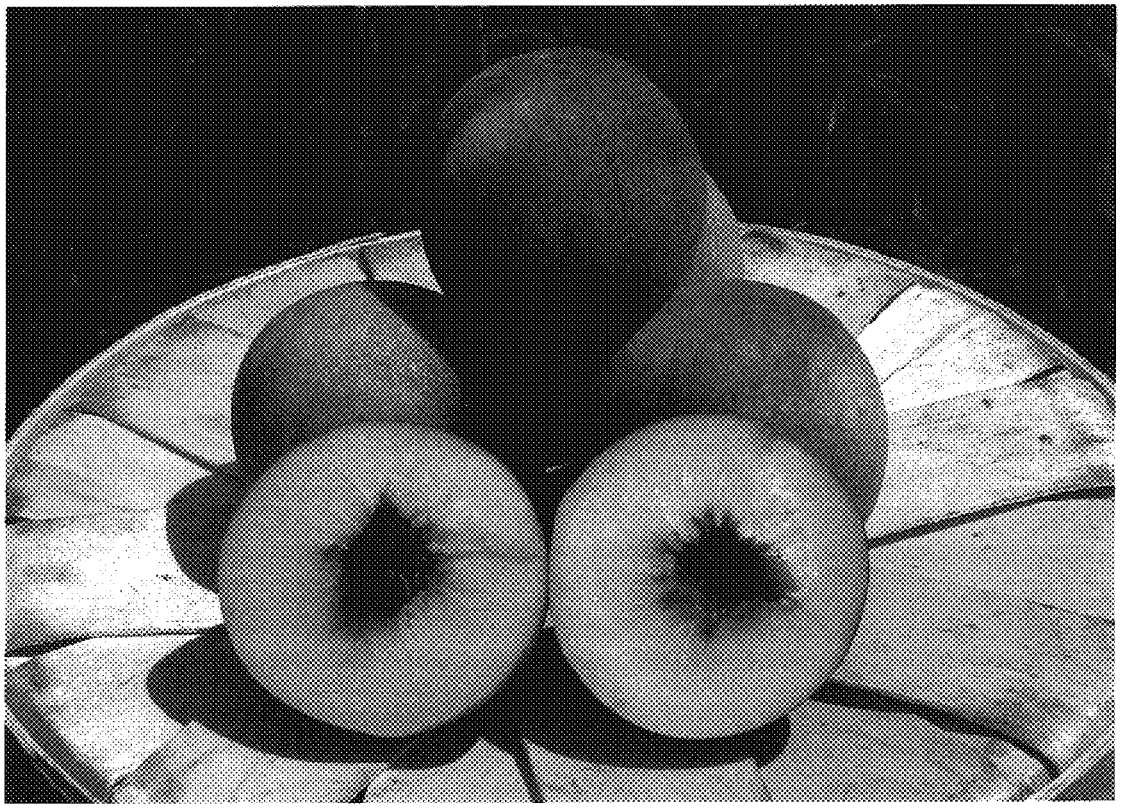
FIG. 1 shows typical fruit of 'Carolina Gold', showing the yellow flesh with minimal red pigmentation around the stone, and the typical skin coloration.
Figure 2:
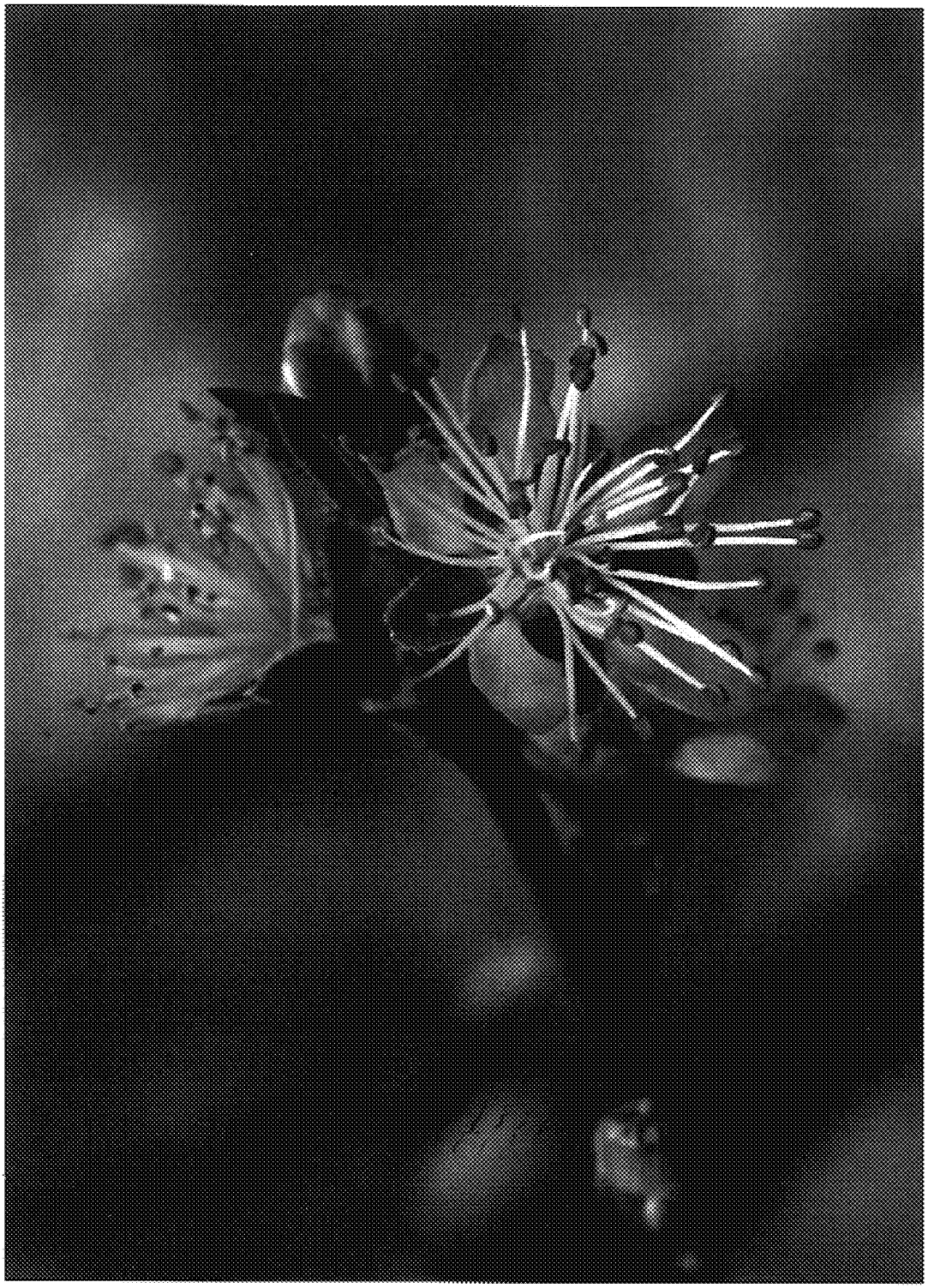
FIG. 2 shows the typical non-showy flower of 'Carolina Gold'.
Figure 3:
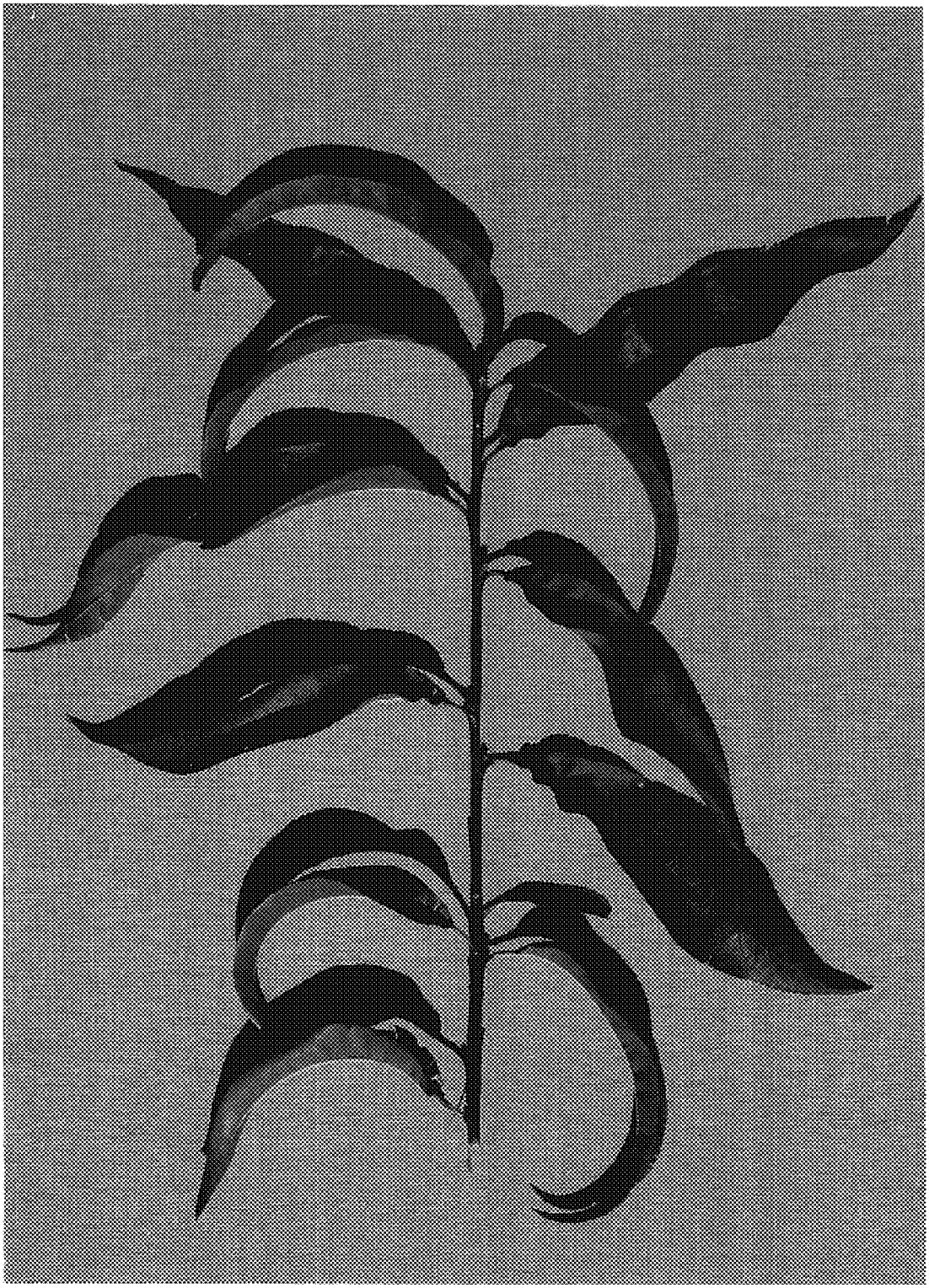
FIG. 3 shows the typical coloration and form of leaves of 'Carolina Gold' taken from a four-year-old tree photographed in September 2004. This figure shows the upper leaf surface.
Figure 4:
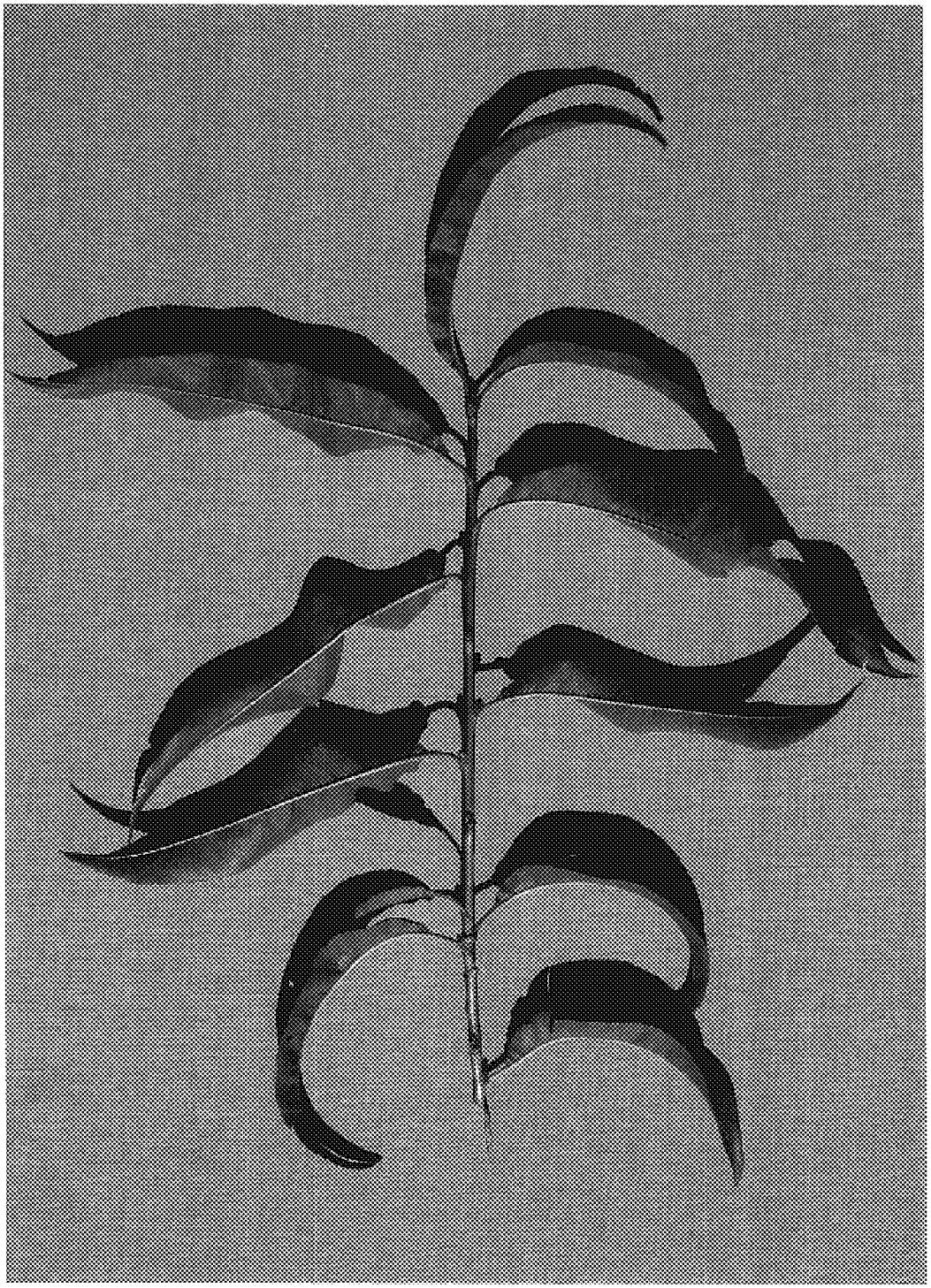
FIG. 4 shows the coloration of the lower leaf surface of leaves of 'Carolina Gold' photographed in September 2004.
Figure 5:
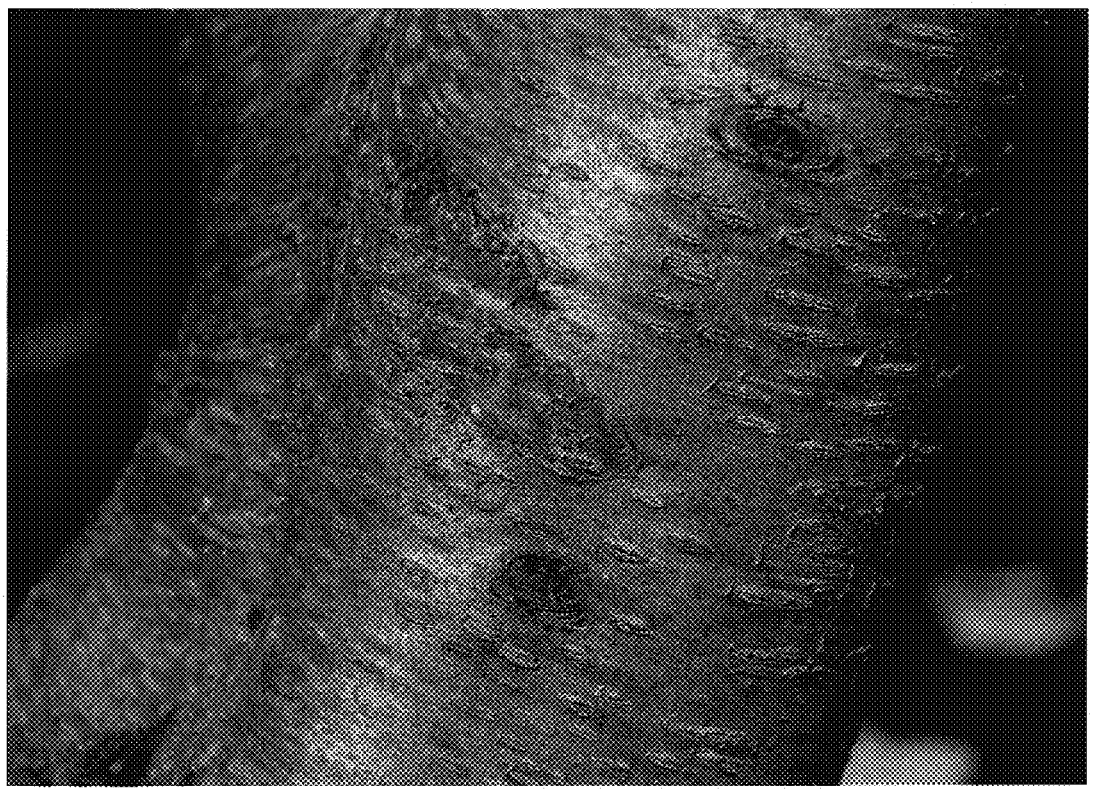
FIG. 5 shows a photograph of the trunk of 'Carolina Gold' taken 1 ft. above the soil line.
Figure 6:
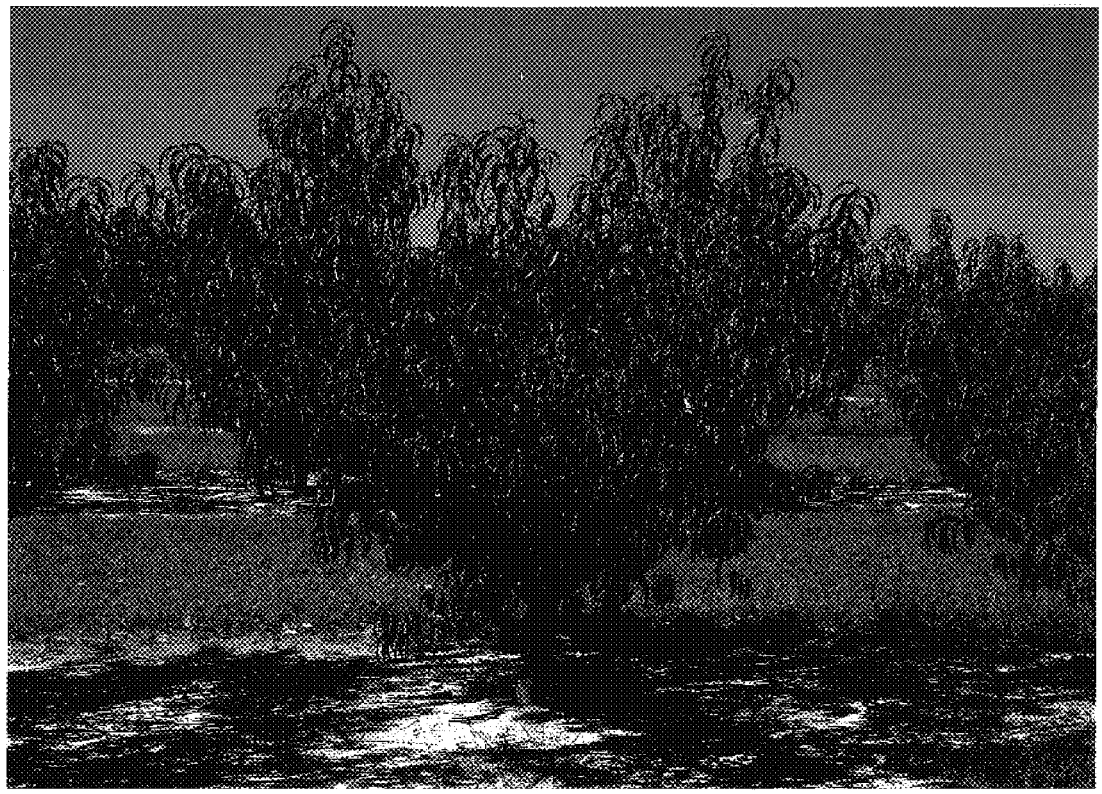
FIG. 6 shows a four-year-old tree of 'Carolina Gold' photographed in September 2004.

The following is a detailed description of the botanical and pomological characteristics of the subject peach. Color data are based on The Royal Horticultural Society Colour Chart, The Royal Horticultural Society, London, 1995 edition. Where dimensions, sizes, colors and other characteristics are given, it is to be understood that such characteristics are approximations of averages set forth as accurately as practicable.

The descriptions reported herein are from four-year-old specimens grown at Jackson Springs, N.C.

Classification: Tree.
Type: Deciduous.
Commercial classification: 'Carolina Gold' serves as a fruit tree that produces high quality peaches for fresh consumption or home canning.
Use: Fruit production.
Tree:
- *Size.*—Large. Four-year old tree average height 8.4 ft. Spread 7.8 ft.
- *Vigor.*—Very vigorous.
- *Growth.*—Semi-upright.
- *Production.*—High. Full crop produced yearly in seven years of observation.
- *Crotch angles.*—Average branch angle between trunk and main branches 55 degrees.

Trunk:
- *Size.*—Circumference=11.1 in. (measured 12 inches above soil).
- *Texture.*—Medium to rough.
- *Color.*—Gray-brown (RHS201B).
- *Lenticels.*—Length=5 mm. Width=2 mm. Shape=oval. Grayed-orange (RHS 165C.).

Branches:
- *Size.*—Medium.
- *Surface.*—Smooth (new) to medium rough (old).
- *Lenticels.*—Length=1 mm. Width=0.5 mm. Shape=oval. Grayed orange (RHS 164C).
- *Color.*—Bright yellow-green (RHS145B, new growth—lower surface), red (RHS53B, new growth—upper surface), grayish-orange (RHS165B, two-year-old branches).

Foliage:

*Length.*—Large. Mature leaf length 15.9 cm; width 3.6 cm.

*Form.*—Lanceolate. Acutely pointed. Base=attenuate.

*Thickness.*—Medium.

*Texture.*—Smooth to slightly rugose.

*Margin.*—Crenate.

*Petiole.*—Medium length, average=9.2 mm. Yellow-green (RHS145C).

*Glands.*—Average number 4. Varies from 2 to 6. Located on base of leaf and upper portion of petiole. Shape=reniformis (oval). Yellow-green (RHS145A). Length=2.3 mm. Width=1.2 mm.

*Color.*—Upper surface — yellow green (RHS146A). Lower surface — yellow green (RHS146B).

*Pubescence.*—Lacking.

Flower buds:

*Size.*—Medium. Typical of peach.

*Width.*—Medium. (3.0 mm).

*Length.*—Medium. (3.0 mm).

*Pubescence.*—Lacking.

*Color before opening.*—Grey-green (RHS190A).

Flowers:

*Date of first bloom.*—March 10 to March 30. Varies yearly due to weather conditions.

*Size.*—Small, non-showy. Diameter=25.2 mm. Varies from 24 to 26 mm.

*Color.*—Petals medium pink (RHS52C). Calyx grayed purple (RHS183C).

*Reproductive organs.*—Stamens — erect, numerous. Average number 42.2. Filament color — red-purple (RHS63C). Pistils — usually one. Color grayed-yellow (RHS162B) Pollen — normal and abundant, yellow-orange (RHS14A).

*Pollination requirements.*—Flowers self-fertile.

*Number of flowers per bud.*—One.

*Number of petals per flower.*—Average 5.

*Pedicel.*—Long (10.6 mm). Color RHS142C.

*Fragrance.*—None detectable.

*Sepals.*—Length=6.1 mm. Width=4.4 mm (base) and 2.9 mm (apex). Shape=ovate with rounded apex.

Fruit:

*Maturity.*—Late. Late July to early August. Average August 1.

*Size.*—Very large. Average 2.8 in. transverse diameter. Average 2.9 longitudinal diameter.

*Weight.*—Average=7.1 ounces.

*Form.*—Round.

*Suture.*—Shallow to slightly grooved.

*Pubescence.*—Light.

*Skin.*—Color=50% red overcolor (RHS34A) with yellow-orange ground color (RHS15B). Thickness=0.024 mm. Slight tendency to crack. Texture=slightly rugose.

*Flesh color.*—Yellow-orange (RHS15C), with little red intrusion (RHS46C) near the pit.

*Flesh texture.*—Smooth, firm, melting.

*Aroma.*—Slight.

*Stone.*—Large, freestone. Color grayed-orange (RHS175B). Size=30.9 mm length, 15.2 mm transverse diameter, 19.8 mm width. Shape=oval. Surface texture=rough. No tendency to crack. Apex shape=pointed. Base shape=attenuate.

*Pit cavity.*—Width=25.6 mm. Length=38 mm. Shape=oval. Color=red (RHS44A).

*Kernel (seed).*—Shape=elliptic. Width=11.25 mm. Length=20 mm. Depth=5 mm. Color (seed coat)=grayed-orange (RHS164C). Color (seed)=orange-white (RHS159D).

*Flesh pH.*—3.6 (soft ripe fruit).

*Soluble solids.*—Average of 5 fruit=11.7 Brix.

*Eating quality.*—Excellent.

*Uses.*—Fresh consumption and home canning.

*Browning potential.*—Low, based on laboratory testing.

Disease reaction:

*Bacterial spot.*—Highly resistant based on field observation.

*Peach scab.*—Susceptible.

*Brown rot.*—Susceptible.

Herbarium voucher: A voucher of 'Carolina Gold' will be deposited into the Herbarium of North Carolina State University (NCSU) in Raleigh, N.C., USA upon patenting.

That which is claimed is:

1. A new and distinct variety of peach tree (*Prunus persica* (L.) Batsch) substantially as illustrated and described, characterized by its very large, yellow flesh fruit, its late flowering, its high resistance of the fruit flesh to browning after slicing, and its high resistance to bacterial spot disease.

* * * * *